United States Patent [19]
Colombo et al.

[11] Patent Number: 5,549,913
[45] Date of Patent: Aug. 27, 1996

[54] MULTILAYER MATRIX SYSTEMS FOR THE CONTROLLED RELEASE OF ACTIVE PRINCIPLES

[75] Inventors: Paolo Colombo; Antonio C. Cardona; Giorgio Pifferi, all of Milan, Italy

[73] Assignee: Inverni Della Beffa S.p.A., Milan, Italy

[21] Appl. No.: 153,437

[22] Filed: Nov. 16, 1993

[30] Foreign Application Priority Data

Nov. 17, 1992 [IT] Italy ................... MI92A2617

[51] Int. Cl.$^6$ ...................................................... A61K 9/24
[52] U.S. Cl. ................................ 424/472; 424/458
[58] Field of Search ................................ 424/486, 487, 424/472, 426, 428, 471, 480, 482

[56] References Cited

U.S. PATENT DOCUMENTS 4,869,908  9/1989  Kirschner et al. ................. 424/472
5,085,865  2/1992  Nayak ............................. 424/472

Primary Examiner—Edward J. Webman
Attorney, Agent, or Firm—Bucknam and Archer

[57] ABSTRACT

This invention concerns systems for the release of active principles which are capable of releasing active principle(s) into an aqueous medium at a controlled rate.

More precisely, the invention concerns a monolithic system for the controlled release of active principles, consisting of:
  a) at least one swelling layer containing one or more active principles, in a matrix of swellable, hydrophilic polymers;
  b) at least one erodible and/or soluble layer comprising excipients and/or water soluble polymers, possibly containing one or more active principles, either the same or different from those present in the layer a), the said erodible and/or soluble layer being in contact with the swelling layer(s) a).

15 Claims, 6 Drawing Sheets

5,549,913

MULTILAYER MATRIX SYSTEMS FOR THE CONTROLLED RELEASE OF ACTIVE PRINCIPLES

FIELD OF THE INVENTION

Monolithic systems for the controlled release of drugs administered orally, are widely used both in human and veterinary therapy. The most widely used monolithic systems are matrix systems consisting of polymeric supports of more or less hydrophilic nature, within which the active principles are dissolved or dispersed. The geometry of these matrices, prepared by compression, and the structural characteristics of the polymers used, control the release of the active principles.

BACKGROUND OF THE INVENTION

In the case of matrices consisting of a swelling hydrophilic polymer, the penetration of the dissolution fluid into the system gives rise to a polymer phase transition from glassy to rubbery state. This transition implies a distension of the polymeric chains which acquire great mobility and the formation of an increasing layer of gelled polymer. Diffusion of the active principle molecules takes place through the gelled layer, whereas this does not occur in the glassy state. The release kinetic of this matrix system is mainly related to diffusion, besides swelling and erosion. In most cases, release rate is a function of the square root of time and therefore tends to decrease as the thickness of the gelled polymeric layer and hence the thickness of the layer that the drug must cross in order to reach the dissolution fluid, increases with the time. A remarkable increase of the external surface of the system occurs because of the swelling and this effect contributes to increase the release rate. Nevertheless the overall observed result is a decreased drug release rate, more and more significant as the end of the release process is approached because of the prevailing effect of the increasing thickness of the gelled layer with the time.

Conventional matrix systems release the active principle more slowly and at a decreasing rate. They consequently do not overcome the disadvantages of traditional pharmaceutical forms, such as a peak of hematic concentration, followed by a relatively sudden fall.

There have been attempts to overcome these drawbacks, which are typical of hydrophilic matrices and related to a non-linear release kinetic. For example, in U.S. Pat. No. 4,839,177, a system is described which consists of a nucleus containing the drug and swelling polymer, having a defined shape, with an insoluble coating on one or more of its faces. The purpose of the coating is to modulate the swelling of the polymer so as to obtain a constant drug release. The system releases the drug with a constant kinetic only in cases where a base or the lateral surface are coated so as to delimit the releasing area. Moreover, the linear kinetic release is obtained only by using soluble polymers.

SUMMARY OF THE INVENTION

The systems of the present invention allow the release of active principle at a constant rate, thanks to a geometry that varies during the release process. During the dissolution, the geometrical modifications of the claimed system are such as to determine a further and gradual increase in total release surface which compensates the reduction of release rate caused by the increase of gelled layer thickness.

Thanks to this system, it is possible to release one or more active principles contained in the monolithic system with a zero order kinetic, such as to maintain constant hematic concentrations.

According to a first preferred aspect, the invention gives three-layer monolithic systems consisting of two external swelling layers separated by an interposed soluble layer.

According to another preferred aspect, the invention gives two-layer monolithic systems consisting of a swelling layer adjacent to a soluble and/or erodible layer.

Examples of hydrophilic swelling polymers which can be used according to the invention include: methylcellulose, carboxymethylcellulose sodium, crosslinked carboxymethylcellulose sodium, crosslinked hydroxypropylcellulose, high, medium and low molecular weight, hydroxy-propyl methylcellulose, carboxymethyl starch, polymethacrylate, polyvinylpyrrolidone (crosslinked or not), high, medium and low molecular weight, polyvinyl alcohols, polyoxyethylene glycols, potassium methacrylate-divinyl benzene copolymer and their mixtures, in proportions between 5% and 70% by weight.

On the other hand, the soluble and/or erodible layer consists of soluble excipients, such as saccharides and polyalcohols, sometimes mixed with polymers selected from hydroxyethylcellulose, carboxymethylcellulose, alginates, albumin, soluble starch and gelatin in proportions up to 20% by weight.

Clearly, other excipients conventionally employed in pharmaceutical technology can be included in the monolithic systems of the invention, such as buffering agents, preservatives, lubricants and acid, basic or amphoteric substances. Examples of these excipients include spray-dried lactose, mannitol or other polyalcohols, talc and magnesium stearate or other lubricants. Active principles can be present in each layer in weight proportions according to their specific activity.

Monolithic systems of the invention can be prepared using conventional techniques, for example by simultaneous compression of the layers or by joining together two or more layers which have been individually prepared.

BRIEF DESCRIPTION OF THE DRAWINGS

The invention will now be described with reference to the attached Figures, where.

Figure 1A:
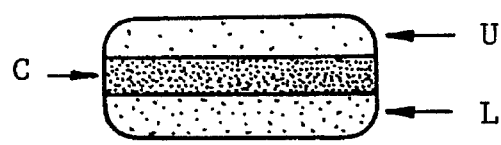
FIG. 1a shows a cross section of a three-layer monolithic system in which the upper, central and lower layers are marked by the letters U, C and L respectively.
Figure 1B:
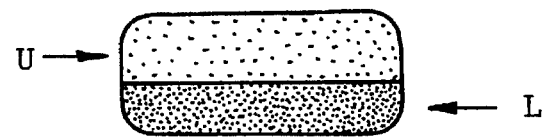
FIG. 1b shows a cross section of a two-layer monolithic system in which the upper and lower layers are marked by the letters U and L respectively.

Both in the cases of FIG. 1a and FIG. 1b, each layer consists of a polymer which can include the active principle to be released and/or other excipients with the function of controlling the release.

In the case of FIG. 1a, layers U and L consist of a mixture containing a hydrophilic polymer and the active substance(s). On the other hand, layer C consists of a mixture of a soluble and/or erodible polymer, or a soluble excipient, in which an active principle may be added if desired.

Placing one of these systems in contact with the aqueous dissolution medium, the U and L layers, consisting of hydrophilic, swelling polymer, take up water to form a growing layer of gel and the system swells. In this way, the drug can be released with a mainly diffusive but also partly convective mechanism, governed by the distension of the polymeric chains. At the same time the C layer begins to disappear by dissolution and/or erosion.

The progressive disappearance of the central C layer brings about an increase in the surface of the external gelled layers exposed to solvent action, an increase added to that caused by the swelling of the U and L layers.

The decrease of the release rate with time, due to the increased thickness of the gelled layer of the U and L layers, is therefore compensated by the fact that the erosion and/or dissolution of the C layer brings about an increase in the releasing area, allowing contact of the solvent with the internal surfaces of the U and L layers. After a certain period of time, mostly related to the composition of the C layer, the separation of the U and L layers takes place.

Figure 2A:
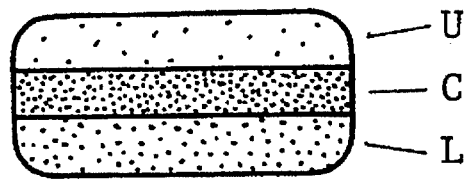
FIG. 2a, FIG. 2b and FIG. 2c shows a schematic drawing of the evolution of the system of in FIG. 1a during the release process.
Figure 2B:
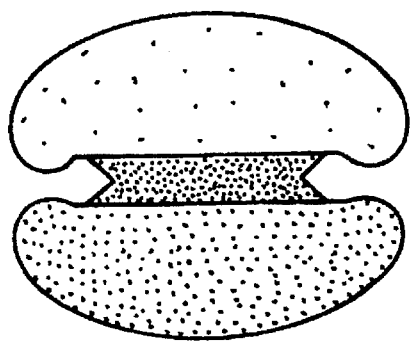
Figure 2C:
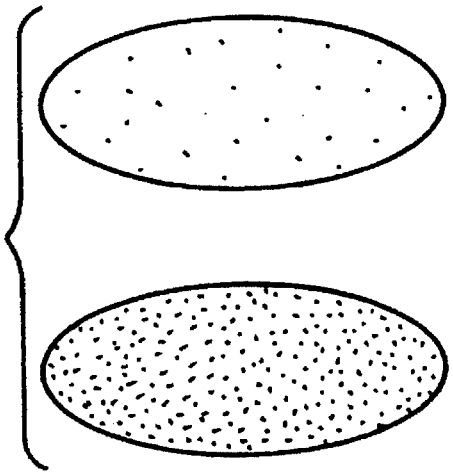

A schematic drawing of the system evolution during the release process is shown in FIG. 2, where the release area increases in time as a result of the disappearance of the C layer.

Therefore, the main aspect of this invention is that the C layer plays the rô of controller of the release of active principles incorporated in the U and L layers. If another active principle is previously included in the C layer, its release is controlled by the erosion and/or dissolution of the layer itself. This system, characterized by remarkable flexibility, allows a wide range of applications in order to obtain suitable release kinetic in the following cases:

a) one active substance subdivided between the U and L layers;

b) two active substances, one subdivided between the U and L layers and the other one incorporated in the C layer, or alternatively, one in the U and the other one in the L layer;

c) three active substances, one in each layer.

By suitably adjusting the polymer quantities in the three layers, it is possible to balance the increase in thickness of the gelled layer of the U and L layers and the erosion and/or dissolution of the C layer. The increase in external surface area will compensate reduced release due to the increase in thickness of the gelled layer, thus allowing a kinetic of zero order. According to the type and proportion of swelling polymers and of active principles in the external U and L layers, a polymer could if necessary be included in the central C layer to delay the dissolution and/or erosion process.

In the case of FIG. 1b the U layer consists of a mixture of a hydrophilic polymer and an active principle. On the other hand, the L layer consists of a mixture of a soluble and/or erodible polymer, or a soluble excipient, in which an active principle, the same or different from the one in the U layer, may be added.

When one of these systems comes in contact with the aqueous dissolution medium, the U layer takes up water, giving rise to a gel of increasing thickness. If a swellable hydrophilic polymer is used, the system swells. In this way, the drug will be released mainly by a diffusion mechanism, in part governed also by distension of the polymeric chains. At the same time the L layer begins to disappear by dissolution and/or erosion. The progressive disappearance of the L layer gives rise to an increase in surface area of the gelled U layer exposed to the action of the solvent, added to that due to the swelling of the U layer itself.

Reduction of release rate, due to the increase in thickness of the gelled layer of the U layer, is therefore balanced by the erosion and/or dissolution of the L layer bringing about an increase in release surface area. This allows solvent contact with that part of the surface of the U layer initially coated by the L layer. If an active principle is incorporated in the L layer, its release is controlled by the erosion and/or dissolution of the layer itself. After a certain time period, mostly related to the composition of the L layer, the complete dissolution of this layer is observed and only the U layer remains, evolving as a simple matrix.

Figure 3A:
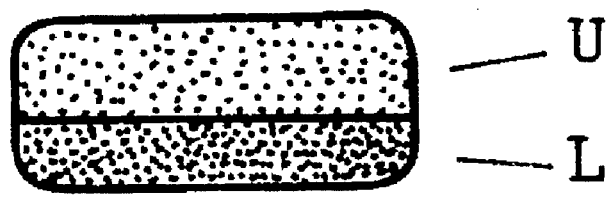
FIG. 3a, FIG. 3b and FIG. 3c shows a schematic drawing of the evolution of the system of FIG. 1b during the release process.
Figure 3B:
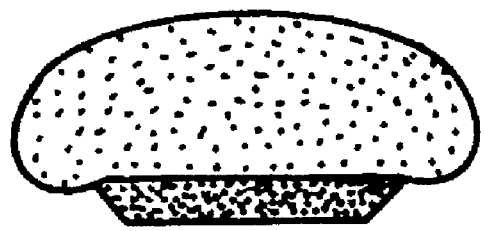
Figure 3C:
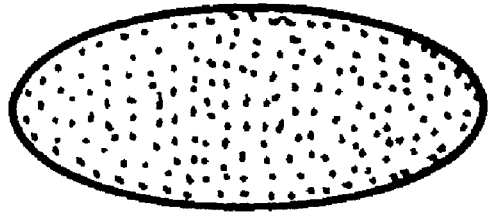
Figure 4A:
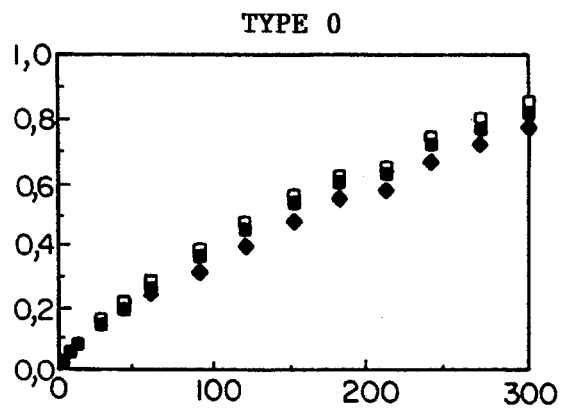
FIG. 4a, FIG. 4b, FIG. 4c, FIG. 4d and 4e illustrates the release profiles of the systems described in Example 1.
Figure 4B:
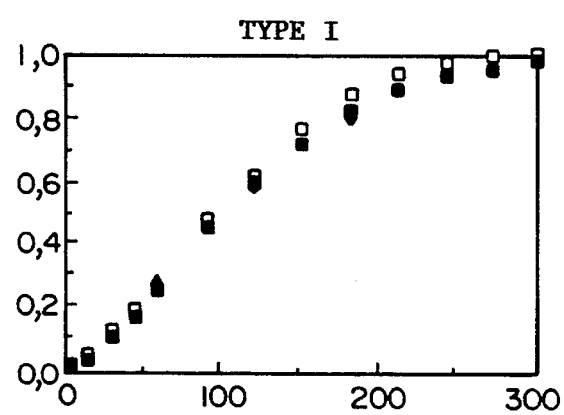
Figure 4C:
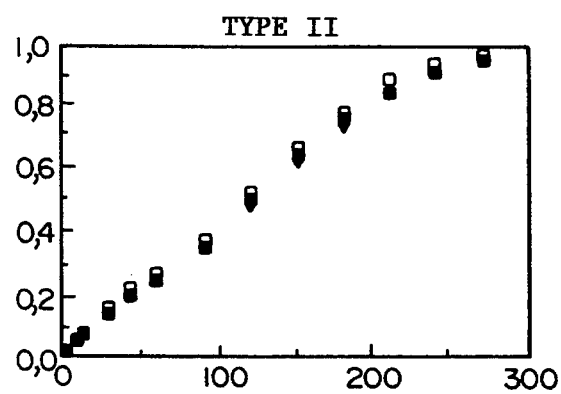
Figure 4D:
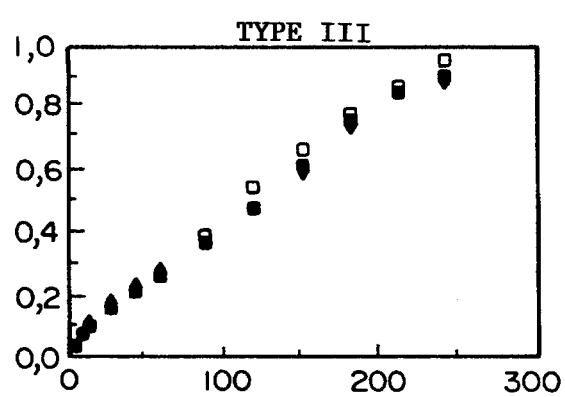
Figure 4E:
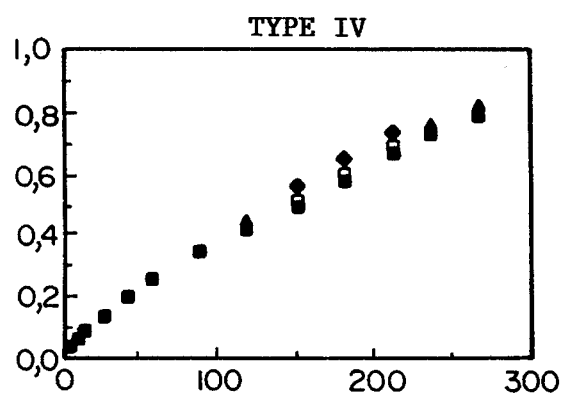

A schematic drawing of the evolution of the system during the release period is shown in FIG. 3, where the release area increases in time as a result of the disappearance of the L layer.

The following examples illustrate some multilayer matrix systems, according to the invention, which have the typical form of a flat or biconvex double- or three-layer tablet with or without break-line, prepared by simultaneous compression or by joining two or more individually prepared layers. The dosage unit can sometimes consist of a group of monolithic systems contained in a hard gelatin capsule.

EXAMPLE 1

Preparation of a three-layer matrix system containing 100 mg of Atenolol subdivided between the U and L layers.

a) Preparation of Granulate for the U and L Layers 400 g of granulate contains:

| | |
|---|---|
| Atenolol (active principle) | 100 g |
| Cellulose acetate phthalate | 8 g |
| Talc | 80 g |
| Hydroxypropyl methylcellulose | 75 g |
| Mannitol | 128 g |
| Magnesium stearate | 4 g |
| Silicon dioxide | 5 g |

The active principle and part of the talc (50 g) were blended in a powder mixer until homogeneous mixture was obtained.

The cellulose acetate phthalate was dissolved in 560 ml of a 1:2 mixture of ethanol and acetone and used to wet the above powder mixture. The mass was then granulated on a 800 μ screen, dried and calibrated through a 600 μ screen. The granulate thus obtained was mixed with the other powders, previously blended.

b) Preparation of Granulate for the C Layer

Four different mixtures were prepared, three of which containing increasing concentrations of a soluble polymer (hydroxyethylcellulose) and inert excipients.

200 g of granulate contains:

| Type I | |
|---|---|
| Spray-dried lactose | 176 g |
| Magnesium stearate | 2 g |
| Talc | 22 g |

In this case the powders are blended to obtain a homogeneous mixture.

| Type II | |
| --- | --- |
| Spray-dried lactose | 176 g |
| Hydroxyethylcellulose | 5 g |
| Talc | 15 g |
| Magnesium stearate | 4 g |

In this case, the lactose, part of the talc (10 g) and the hydroxyethylcellulose are blended to homogeneity. The mixture is then wetted with water and granulated on a 800 μ screen. After drying the granulate is calibrated through a 600 μ screen and then mixed with the magnesium stearate and the remaining talc (5 g),

| Type III | |
| --- | --- |
| Spray-dried lactose | 171 g |
| Hydroxyethylcellulose | 10 g |
| Talc | 15 g |
| Magnesium stearate | 4 g |

The same procedure is used as for Type II

| Type IV | |
| --- | --- |
| Spray-dried lactose | 161 g |
| Hydroxyethylcellulose | 20 g |
| Talc | 15 g |
| Magnesium stearate | 4 g |

The same procedure is used as for type II c) Preparation of Three-layer Tablets

The systems described in this example were obtained using a reciprocating tabletting machine (Model EKO, Korsch, Berlin) and flat punches of 11.3 mm diameter for the simultaneous compression of three layers, respectively:

L layer consisting of 200 mg of granulate as point a) above;

C layer consisting of 200 mg of mixture as point b) above;

U layer consisting of 200 mg of granulate as point a) above.

By varying the C layer (types I, II, III and IV), different release profiles were obtained: it was noted that the optimum polymer concentration in the C layer, to obtain a kinetic of the zero order, is that of case III.

As reference, simple matrices were prepared by compression, consisting of a single layer of 400 mg of the granulate as point a), therefore equivalent to the whole of the U and L layers of the three-layer matrix (type O).

d) In Vitro Active Principle Release Tests

In vitro tests were carried out on the three-layer systems and on the one-layer matrices used as reference. The dissolution apparatus described in US Pharmacopoeia XXII <711>, pages 1578–9, Apparatus 2, was used for these determinations, with a paddle rotation speed of 125 rpm. A square screen (l=33 mm; openings 1.25 mm) was placed on the bottom of the dissolution vessel to prevent the tablets from sticking to it. Distilled water at 37° C. was used as dissolution medium.

The amount of active principle released was spectrophotometrically determined at 224.5 nm in a 1 mm continuous flow cell, at 5–10–15–30–45–60–90 minutes and then every 30 minutes until complete release of the active principle.

Results of the in vitro tests are shown in FIG. 4.

The release profiles of the one-layer reference tablets and those of the tablets according to this invention are clearly different. This agrees with the release control function played by the central C layer.

For the type O, one-layer matrices, equivalent to the whole of the U and L layers in the three-layer matrices, dissolution rate decreases after early release phases, as expected. Actually overcoming of this drawback is the target of this present invention.

For the type I, three-layer matrices according to this present invention, in which the soluble C layer does not contain polymers, the release profile has a sigmoid shape owing to too fast a detachment of the U and L layers: as the increase in release surface area is sudden, the release rate increases too quickly.

Using 2.5% of hydroxyethylcellulose (type II) in the C layer, a linearization of the release profile can already be observed. This linearization is almost total in the case of type III, 5% of polymer being incorporated into the C layer: the release rate is practically constant almost till to the end of the release process.

With a further increase of the polymer content in the C layer, the disappearance of the C layer is delayed to such an extent as to obtain a release profile comparable to that of type O.

EXAMPLE 2

Preparation of three-layer matrix systems containing 400 mg of Trapidil subdivided between the U and L layers.

a) Preparation of Granulate for the U and L Layers 550 g of granulate contains:

| Trapidil (active principle) | 400 g |
| --- | --- |
| Hydroxypropyl methylcellulose | 125 g |
| Carboxymethylcellulose sodium | 20 g |
| Magnesium stearate | 5 g |

The first three components were blended in a powder mixer until homogeneous mixture.

A 1:1 mixture of ethanol and water was prepared and used to wet the powder mixture. The mass was granulated on a 800 μ screen, dried and then calibrated through a 600 μ screen. The obtained granulate was then mixed with the magnesium stearate.

b) Preparation of a Mixture for the C Layer

Type I 200 g of mixture contains:

| Spray-dried lactose | 176 g |
| --- | --- |
| Magnesium stearate | 2 g |
| Talc | 22 g |

Simple mixing is carried out to obtain a homogeneous mixture.

c) Preparation of Three-Layer Tablets

The systems described in this example were obtained using a reciprocating tabletting machine (Model EKO, Korsch, Berlin) and concave punches of 12 mm diameter for the simultaneous compression of three layers, respectively:

L layer consisting of 275 mg of granulate as point a);

C layer consisting of 200 mg of mixture as point b);

U layer consisting of 275 mg of granulate as point a).

As reference, simple matrices were prepared by compression, consisting of a single layer of 550 mg of granulate as point a), therefore equivalent to the whole of the U and L layers of the three-layer matrix (type O).

7 d) In vitro Active Principle Release Tests

In vitro tests were carried out on the three-layer systems and on the one-layer matrices used as reference. The dissolution apparatus described in US Pharmacopoeia XXII <711>, pages 1578–9, Apparatus 2, was used for these determinations, with a paddle rotation speed of 125 rpm. A square screen (1=33 mm; openings 1.25 mm) was placed on the bottom of the dissolution vessel to prevent the tablets from sticking to it. Distilled water at 37° C. was used as dissolution medium.

The amount of active principle released was spectrophotometrically determined at 271 nm in a 1 mm continuous flow cell, at 5–10–15–30–45–60–90 minutes and then every 30 minutes until complete release of the active principle.

Figure 5A:
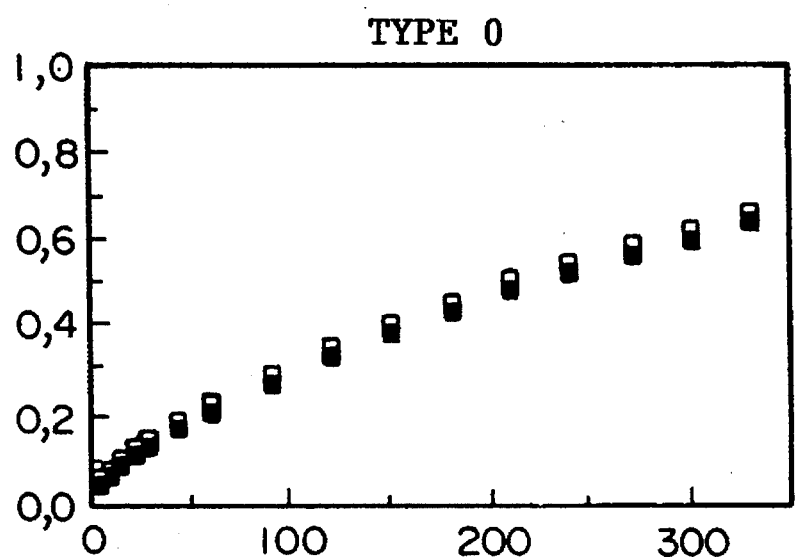
FIG. 5a, and FIG. 5b illustrates the release profiles of the systems described in Example 2.
Figure 5B:
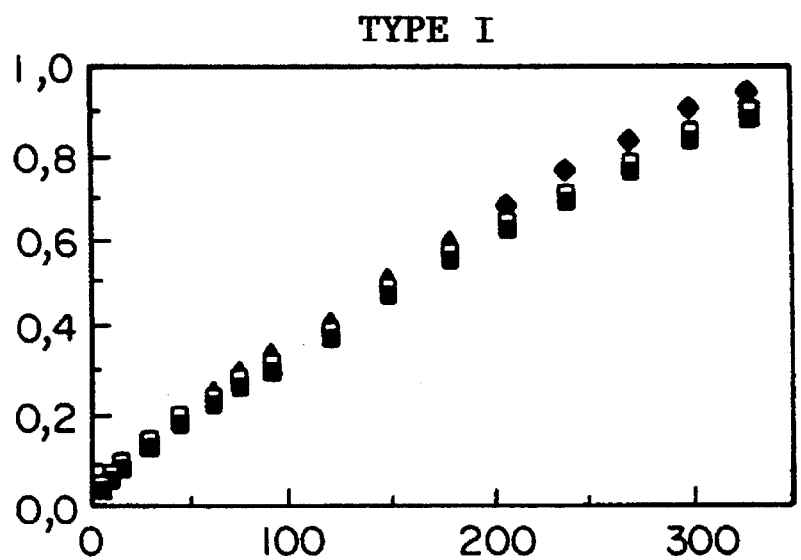

Results of the in vitro tests are shown in FIG. 5.

The release profiles of the one-layer reference tablets and those of the tablets according to this invention are clearly different. This agrees with the release control function played by the central C layer.

For the type O, reference matrices, dissolution rate decreases in time, as expected. Actually overcoming of this drawback is the target of this present invention.

In particular, a quite high initial dissolution rate is observed which decreases progressively.

For the type I, three-layer matrices according to this present invention, the release profile is quite linear, owing to the fast disappearance of the C layer.

EXAMPLE 3

Preparation of monolithic two-layer systems containing 100 mg of Atenolol in the U layer.

a) preparation of Granulate for the U Layer

| | |
|---|---|
| Atenolol (active principle) | 100 g |
| Cellulose acetate phthalate | 8 g |
| Talc | 80 g |
| Hydroxypropyl methylcellulose | 75 g |
| Mannitol | 128 g |
| Magnesium stearate | 4 g |
| Silicon dioxide | 5 g |

The active principle and part of the talc (50 g) were blended in a powder mixer until homogeneous mixture.

A solution of the cellulose acetate phthalate was prepared in 560 ml of a 1:2 mixture of ethanol and acetone and used to wet the above powder mixture. The mass was then granulated on a 800 μ screen, dried and calibrated through a 600 μ screen. The obtained granulate was then mixed with the other constituents, previously blended.

b) Preparation of Granulate for the L Layer (Type I)

200 g of granulate contains:

| | |
|---|---|
| Spray-dried lactose | 171 g |
| Hydroxyethylcellulose | 10 g |
| Talc | 15 g |
| Magnesium stearate | 4 g |

The lactose, part of the talc (10 g) and the hydroxyethylcellulose were blended to homogeneity. The powder mixture was wetted with water, granulated on a 800 μ screen, dried and then calibrated through a 600 μ screen. The obtained granulate was mixed with the magnesium stearate and the remaining talc (5 g).

c) Preparation of Two-Layer Tablets

The systems described in this example were obtained using a reciprocating tabletting machine (Model EKO, Korsch, Berlin) and flat punches of 11.3 mm diameter for the simultaneous compression of two layers, respectively:

8

U layer consisting of 400 mg of granulate as point a);
L layer consisting of 200 mg of mixture as point b).

A reference, simple matrices were prepared by compression, consisting of a single layer of 400 mg of granulate as point a), therefore equivalent to the U layer of the two-layer matrix (type O).

d) In Vitro Active Principle Release Tests

In vitro tests were carried out on the two-layer systems and on the one-layer matrices used as reference. The dissolution apparatus described in US Pharmacopoeia XXII <711>, pages 1578–9, Apparatus 2, was used for these determinations, with a paddle rotation speed of 125 rpm. A square screen (1=33 mm; openings 1.25 mm) was placed on the bottom of the dissolution vessel to prevent the tablets from sticking to it. Distilled water at 37° C. was used as dissolution medium.

The amount of active principle released was spectrophotometrically determined at 224.4 nm in a 1 mm continuous flow cell, at 5–10–15–30–45–60–90 minutes and then every 30 minutes until complete release of the active principle.

Figure 6A:
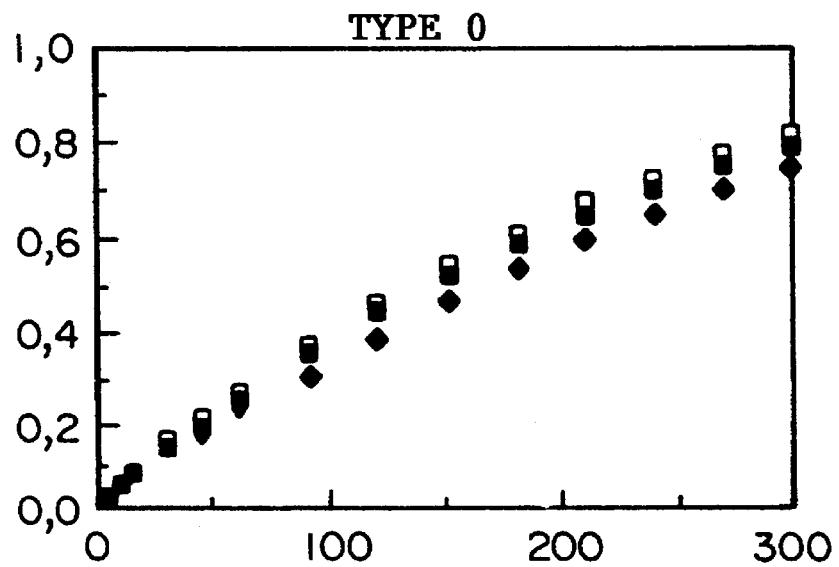
FIG. 6a and 6b illustrates the release profiles of the systems described in Example 3.
Figure 6B:
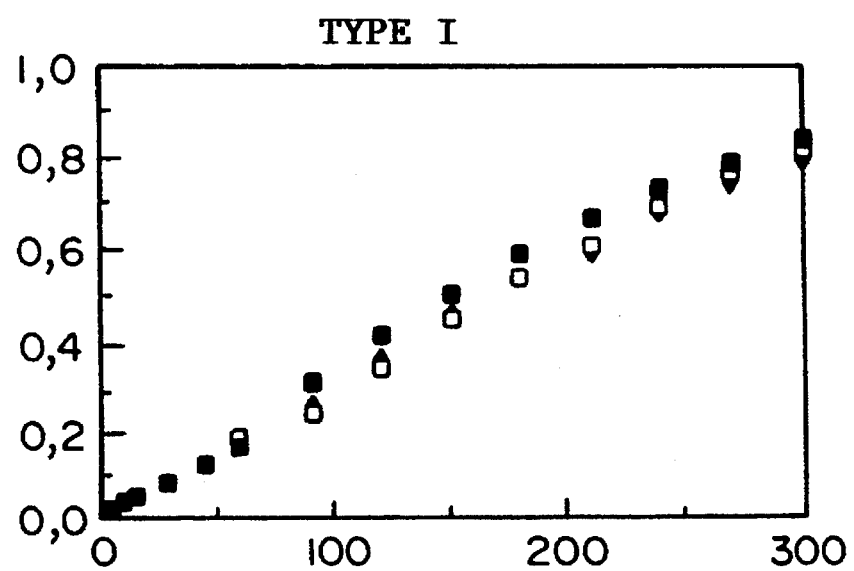

Results of the in vitro tests are shown in FIG. 6.

The release profiles of the one-layer reference matrices and those of the two-layer systems according to this invention are clearly different. This agrees with the release control function played by the L layer. The gradual disappearance of the L layer in the type I matrices, in fact allows a gradual increase of the releasing surface area such as to achieve a constant release rate, unlike what is observed in the case of the reference one-layer matrices (type O).

We claim:

1. A tablet for controlled release of a drug to be administered orally and for release of said drug at a constant rate with zero order kinetic, said tablet comprising two external layers containing 5–70% by weight of the total weight of said tablet of hydrophilic swelling polymers separated by an interposed layer containing a water soluble polymer in the amount of up to 20% by weight of the total weight of said tablet, said drug being mixed with at least one of said external layers containing said hydrophilic swelling polymers, said interposed layer controlling the release of said drug.

2. The tablet according to claim 1 wherein said drug is also mixed with said interposed soluble polymer.

3. The tablet according to claim 2 which is a plain or biconvex tablet, with a break line or is free of a break line.

4. The tablet according to claim 1 wherein said hydrophilic swelling polymer is a member selected from the group consisting of methylcellulose, crosslinked carboxymethylcellulose sodium, crosslinked hydroxypropylcellulose, hydroxypropylmethylcellulose, carboxymethyl starch, polymethacrylate, crosslinked polyvinylpyrrolidone, polyvinylpyrrolidone free of crosslinking, polyvinyl alcohols, polyoxyethylene glycols, potassium methacrylate-divinylbenzene copolymer and mixtures thereof.

5. The tablet according to claim 1 wherein said water soluble polymer is a member selected from the group consisting of hydroxyethylcellulose, alginates, albumin, soluble starch and gelatin.

6. The tablet according to claim 1 which contains one excipient which is a member selected from the group consisting of spray-dried lactose, mannitol, talc, magnesium stearate, lubricants, buffering agents, preservatives and mixtures thereof and said excipient is located in at least one of said external layers and said interposed layer.

7. The tablet according to claim 6 wherein each of said external layers consists of the drug atenolol, cellulose acetate phthalate, talc, hydroxypropyl methyl cellulose, mannitol, magnesium stearate and silicon dioxide and said interposed layer consists of spray-dried lactose, hydroxyethyl cellulose, talc and magnesium stearate.

8. The tablet according to claim 7 which is prepared from atenolol in the total amount of 100 grams and said interposed layer is prepared from 171 grams of spray-dried lactose, 10 grams of hydroxyethyl cellulose, 15 grams of talc and 4 grams of magnesium stearate and after compression of two external layers and said interposed layer, the compressed msterial is tabletted.

9. The tablet according to claim 6 wherein each of said external layers consists of trapidil, hydroxypropyl methyl cellulose, carboxymethyl cellulose sodium and magnesium stearate and said interposed layer consists of spray-dried lactose, magnesium stearate and talc.

10. A tablet for controlled release of a drug to be administered orally and for release at a constant rate of said drug with zero order kinetic comprising layer a) a hydrophilic swelling polymer in the amount of 5–70% by weight of said tablet, and layer b) a water soluble polymer in the amount of up to 20% by weight of said tablet, said drug being mixed with at least one of layer a) and layer b), said layer b) controlling the release of said drug.

11. The tablet according to claim 10 wherein said hydrophilic swelling polymer is a member selected from the group consisting of methylcellulose, crosslinked carboxymethylcellulose sodium, crosslinked hydroxypropylcellulose, hydroxypropylmethylcellulose, carboxymethyl starch, polymethacrylate, crosslinked polyvinylpyrrolidone, polyvinylpyrrolidone free of crosslinking, polyvinyl alcohols, polyoxyethylene glycols, potassium methacrylate-divinylbenzene copolymer and mixtures thereof.

12. The tablet according to claim 10 wherein said water soluble polymer is a member selected from the group consisting of hydroxyethylcellulose, alginates, albumin, soluble starch and gelatin.

13. The tablet according to claim 10 which contains one excipient which is a member selected from the group consisting of spray-dried lactose, mannitol, talc, magnesium stearate, lubricants and mixtures thereof, said excipient being placed in said layer b).

14. The tablet according to claim 13 wherein said layer b) consists of spray-dried lactose, hydroxyethyl cellulose, talc and magnesium stearate.

15. The tablet according to claim 10 which is prepared from atenolol in the total amount of 100 grams and 171 grams of said layer b) which consists of spray-dried lactose, 10 grams of hydroxypropylcellulose, 15 grams of talc, 4 grams of magnesium stearate and after compression of layers a) and b), the compressed material is tabletted.

* * * * *